United States Patent [19]

Goldstein et al.

[11] 4,437,857
[45] Mar. 20, 1984

[54] METHOD AND APPARATUS FOR TRAVERSING BLOOD VESSELS

[75] Inventors: Seth Goldstein, Bethesda, Md.; Robert Jones, Woodbridge, Va.

[73] Assignee: The United States of America as represented by the Secretary of the Department of Health and Human Services, Washington, D.C.

[21] Appl. No.: 22,219

[22] Filed: Mar. 19, 1979

[51] Int. Cl.³ ............................................. A61M 25/00
[52] U.S. Cl. ......................................... 604/53; 604/271
[58] Field of Search ................... 128/262, 348, 349 R, 128/350, 349 B, 349 BV, 656, 658, 692, 772; 604/52–53, 270–273

[56] References Cited

U.S. PATENT DOCUMENTS

| | | |
|---|---|---|
| 3,168,092 | 2/1965 | Silverman . |
| 3,332,424 | 7/1967 | Minteer . |
| 3,433,215 | 3/1969 | Silverman . |
| 3,502,069 | 3/1970 | Silverman ............................ 128/772 |
| 3,525,329 | 8/1970 | Zeimer et al. . |
| 3,583,391 | 6/1971 | Cox et al. . |
| 3,669,099 | 6/1972 | Silverman . |
| 3,687,142 | 8/1972 | Leibinzohn ......................... 128/656 |
| 3,908,663 | 9/1975 | Viek . |
| 3,911,927 | 10/1975 | Rich et al. . |
| 3,982,544 | 9/1976 | Dyck .................................. 128/262 |
| 4,041,948 | 8/1977 | Flam et al. . |
| 4,043,345 | 8/1977 | Kramann et al. . |
| 4,109,659 | 8/1978 | Sheridan ............................. 128/262 |

*Primary Examiner*—C. Fred Rosenbaum
*Attorney, Agent, or Firm*—Holman & Stern

[57] ABSTRACT

Disclosed is a method for obtaining access to a relatively inaccessible region of a blood vessel for diagnostic or therapeutic purposes in which a primary catheter tube is inserted into the vascular system at an entry point remote from the relatively inaccessible region, the leading end of the tube is worked towards the inaccessible region in a conventional manner and then a secondary catheter tube contained within the primary tube is everted from the leading end of the primary tube to approach more closely to the required region. A catheter assembly for performing the method is also disclosed.

2 Claims, 11 Drawing Figures

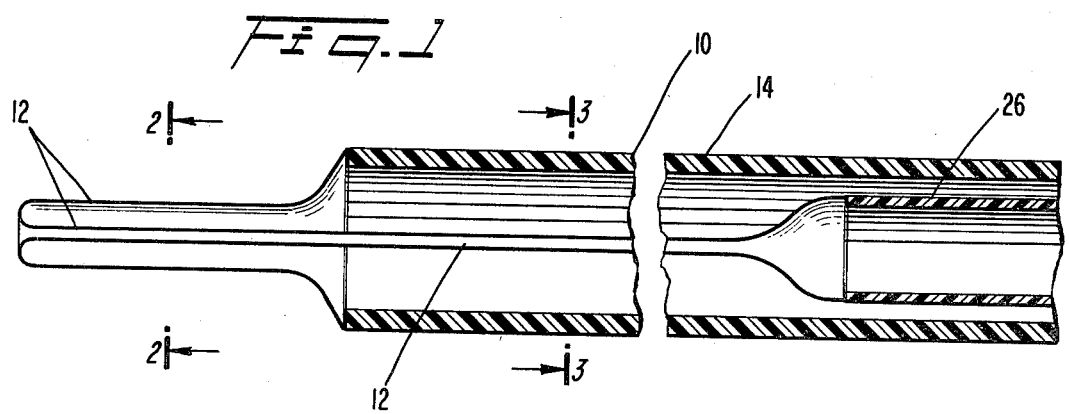
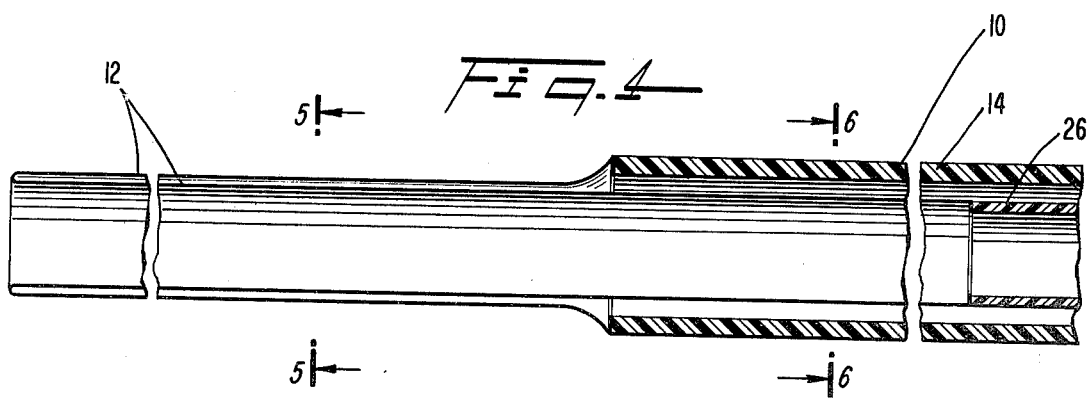

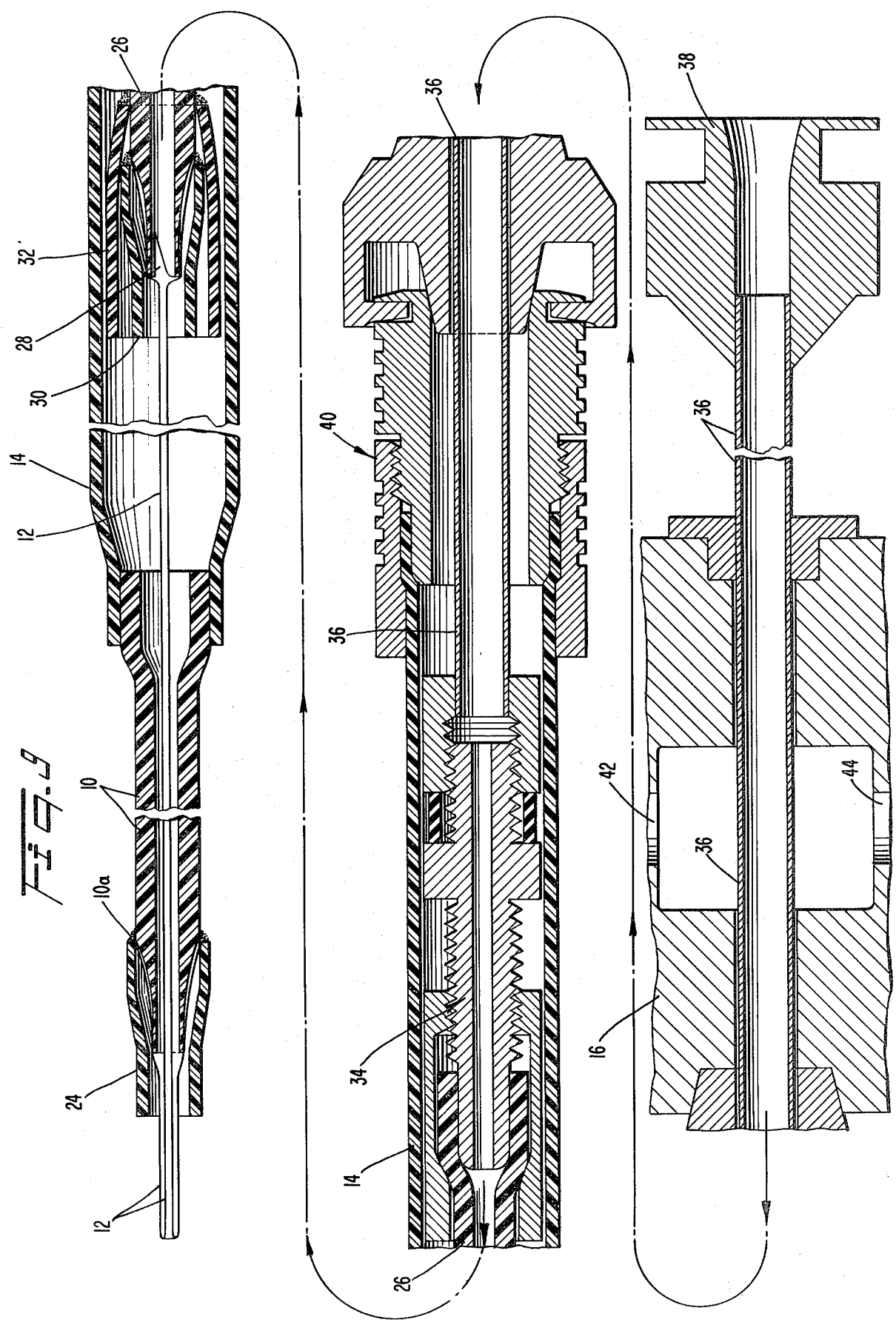

METHOD AND APPARATUS FOR TRAVERSING BLOOD VESSELS

BACKGROUND OF THE INVENTION

In recent years, special purpose catheter systems have been used to traverse and negotiate blood vessels for therapeutic as well as diagnostic purposes. Therapy is delivered via catheters both as an alternative to traditional surgery and as a means of last resort when surgery is not possible. Thus, embolization of selected blood vessels is sometimes performed in order to treat arterio-venous malformations and aneurysms, to block off the blood supply to tumors and to stop chronic bleeding. Other uses of catheters are to deliver chemotherapeutic agents and other substances to highly localized areas and to sample body fluids from remote spaces. More recently, balloon-type catheters have been used for treating stenoses in blood vessels as a means of relieving the constriction by physically expanding the vessel in the region of a stenosis.

Since the usefulness of the above forms of treatment is limited by the accessibility of the lesion to be treated, efforts have been made to develop catheters which can successfully penetrate ever deeper into the vascular system.

The basic problem is to advance a catheter through a narrow tortuous blood vessel without damaging the endothelium. Conventional catheters are often too large to fit inside the desired vessel or too rigid to negotiate the various twists and turns encountered in a particular vessel. Alternatively, they may be so flexible as to buckle instead of advancing into a remote vessel. Friction between the catheter and the vessel wall generally limits the length and number of curves through which a catheter can be pushed and even with balloon tipped catheters, which take advantage of flow to pull the catheters through tortuous vessels, their travel is limited by wall friction. Magnetically guided catheters are similarly limited and their overall complexity and expense limit their widespread application.

It is an object of the present invention to provide a method and apparatus for traversing blood vessels and which allows relatively deep penetration of the vascular system even through narrow and tortuous blood vessels.

More particularly, it is an object of the invention to provide a catheter arrangement particularly suitable for the use in traversing a blood vessel and which at least partially overcomes the problems associated with earlier catheter arrangements used for this purpose particularly as regards the matter of friction between the catheter and the vessel wall.

It is a further object of the invention to provide a catheter arrangement for use in the vascular system which facilitates movement of the catheter through a narrow or tortuous blood vessel to obtain access to relatively remote or inaccessible regions of the vessel.

Another object of the invention is to provide an improved method and means for traversing a blood vessel for therapeutic or diagnostic purposes.

SUMMARY OF THE INVENTION

The invention is based on the concept of adapting the known principle of an everting tube for use in a miniature catheter of a scale sufficiently small to negotiate a blood vessel.

An everting tube is a generally thin-walled flexible tube having a forward end attached to a circular opening in some form of housing, the tube being turned back inside itself to form a double-walled tube and the rear end of the tube (the inner wall) being attached to a moveable member within the housing. With this arrangement, an annular space is formed between the outer and inner walls of the tube. Thus, if the moveable member is caused to move towards the opening and pressure is applied to the annular space, the inner wall of the tube will gradually extend or evert from the opening, "turn the corner" and form an ever lengthening outer wall. There is no movement of the outer wall as such, instead its length is progressively extended by the inner wall as it moves out and "turns the corner". Further, the passageway defined within the inner wall can be used to carry liquid when pressure is released from the annular space.

The everting tube principle has previously been applied to catheters, see for example, U.S. Pat. Nos. 3,525,329, 4,043,345, 3,908,663, 3,332,424, 3,911,927, 3,583,391, 3,669,099, 3,168,092, 3,433,215 and 4,041,948, but such catheters have generally been intended for use in relatively large-scale body passages and would not be suitable for use in an intravascular application requiring extensive penetration along extremely narrow and tortuous vessels.

Two significant advantages over conventional catheters result from the everting tube principle of operation. Firstly, since there is no bodily movement of the outer wall of the tube, there is no relative motion and substantially no friction between the outer wall and the wall of the vessel through which it extends, and secondly, there is no need to make the usual design compromise between catheter rigidity to avoid buckling as it advances and catheter flexibility to negotiate sharp turns in the vessel.

Problems arise, however, in adapting the everting tube principle for use in a catheter system suitable for intravascular use which requires tubes of extremely small diameter (e.g. 1 mm.) and which need to travel relatively long distances through tortuous blood vessels.

The force advancing the everting tube is proportional to the product of the area of the annulus between the inner and outer tube walls and the pressure P within this annulus and small size tubes require high pressure to provide enough force to evert the tube and make it advance. The advancing force must overcome (a) the resistance associated with bending forces where the tube everts or turns on itself, (b) frictional forces of the uneverted portion of the tube sliding through the housing in which it is carried, and (c) frictional forces of the uneverted portions of the tube sliding within itself in the everted length. This last contribution arises mainly from internal contact forces resulting when pressure P is applied, causing the inner wall of the tube to collapse into a ribbon-like form which tends to curl around to fit into the outer wall. If the pressure P is increased too much to overcome the retarding forces, the tubing tends to balloon and burst and if the wall thickness of the tube is increased too much, to prevent bursting, the tube may not readily evert.

In accordance with the present invention, the everting tube principle is applied to an intravascular catheter system by utilizing the tube as a secondary catheter which everts from the leading end of a primary catheter tube. Thus, in use, the primary catheter tube of generally conventional form with the everting tube carried completely inside of it, is inserted into and worked through a blood vessel in the conventional manner and when the leading end of the primary tube has reached the limit of its travel, due either to further inaccessibility or length of travel, the everting tube, having its forward end attached to the leading end of the primary tube, is everted from the leading end of the primary tube for further advancement along the blood vessel.

Further in accordance with the invention, to reduce the friction problems associated with everting tubes of small diameter, as outlined above, the everting tube is made in a particular form, namely the tube, which preferably is extruded from a strong flexible synthetic plastic material and coated with an anti-friction coating, is heat set into a cross-sectional form which ensures that when everted, the inner wall section will fit naturally within the outer wall section without excessive contact force when pressure is applied in the annulus therebetween. Preferably, the tube is heat set to provide a cross section having an indented profile, such as a U-shaped or cruciform profile, the former profile being preferred. Then, in use, the uneverted length of the tube, the inner wall section, retains its heat set indented form while the everted length of the tube due to pressure in the annular space between the sections opens to its natural substantially circular cross-sectional form. After complete eversion of the tube, when pressure is released from the annular space and fluid is passed through the central tube passageway within the uneverted length, this uneverted section will, in turn, open out to assume the natural cross-sectional form due to the fluid pressure within it.

Other features of the invention will become apparent from the ensuing description taken in conjunction with the accompanying drawings.

BRIEF DESCRIPTION OF THE DRAWINGS

FIGS. 2 and 3 are sections on lines 2—2 and 3—3 of FIG. 1, respectively;

FIG. 4 is a view similar to FIG. 1, showing the everting tube in a fully extended condition and with its inner wall inflated;

FIGS. 5 and 6 are sections on lines 5—5 and 6—6 of FIG. 4, respectively;

FIG. 7 is a perspective view of a complete catheter assembly;

FIG. 9 is a composite cross-sectional view of the entire assembly shown in FIG. 7.

DESCRIPTION OF THE PREFERRED EMBODIMENT

Figure 1:
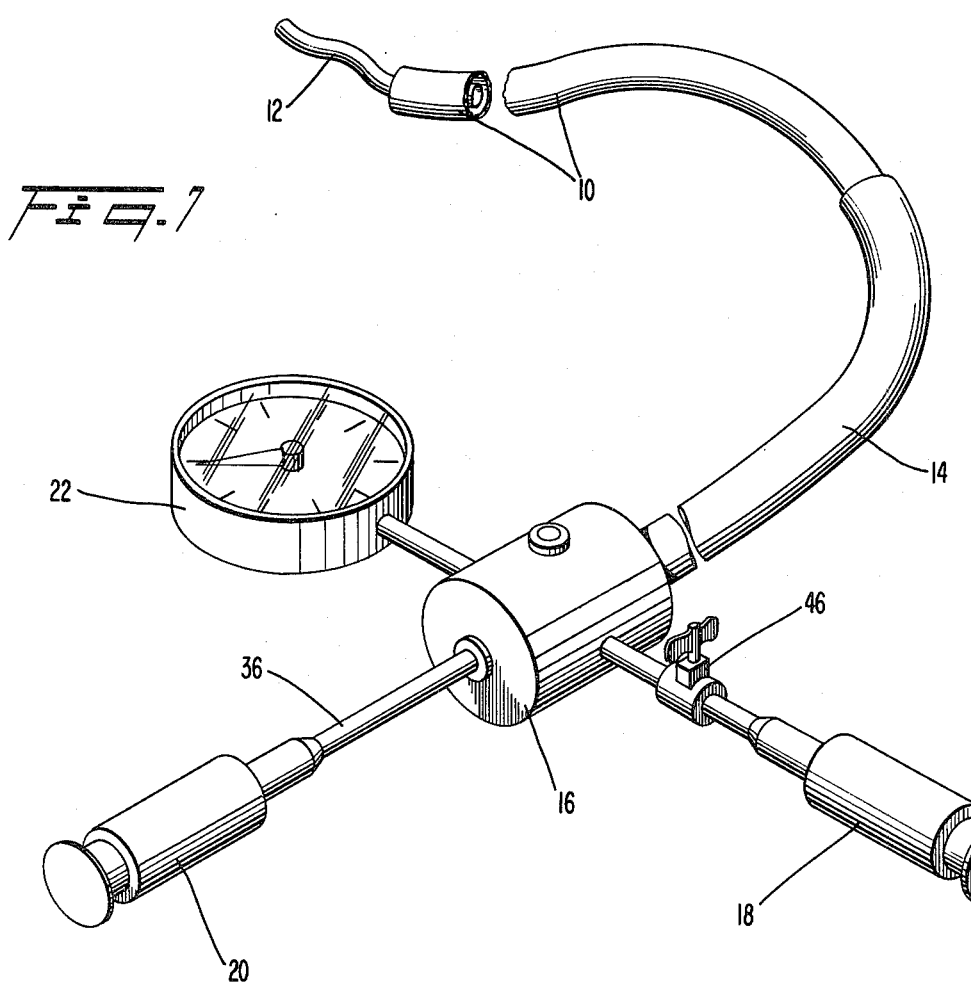
FIG. 1 is a schematic cross-sectional view through the forward end of a catheter system incorporating an everting tube and showing the everting tube in a partially extended condition.
Figure 8:
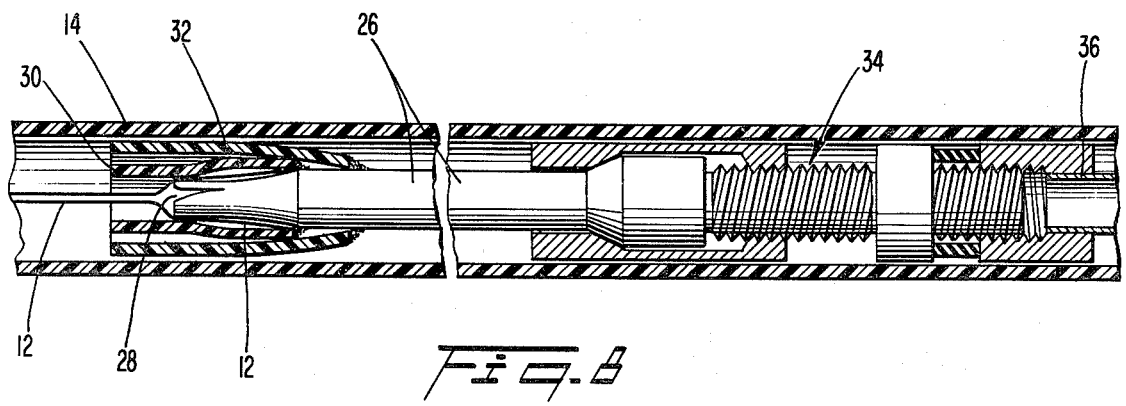
FIG. 8 is a cross-sectional view of part of the assembly shown in FIG. 7.

As best shown in FIG. 7, the principal components of the illustrated catheter assembly are a primary catheter tube 10 and an everting tube 12, these being the components which actually enter the vascular system of a patient and the assembly being completed by ancilliary equipment remaining external to the patient's body and including an extension tube 14, a manifold 16, syringes 18 and 20 for applying pressure fluid respectively to the outer annulus of the everting tube and to its internal passageway, and a pressure gauge 22 for measuring the pressure of the former fluid. In use, the primary catheter tube 10 with the everting tube 12 fully contracted therewithin is inserted into the vascular system and worked along a blood vessel in the conventional manner. Then, when the leading end of the tube 10 has reached its limit of travel through the blood vessel, tube 12 is everted from within tube 10 for further advancement of the catheter along the vessel.

Tube 10 is a conventional form of flexible catheter tubing used for intra-vascular applications for example, a polyurethane tube of 2.15 mm. outside diameter, 1.4 mm. inside diameter and 1 meter long, the tube having its inner surface treated with a friction reducing hydromer coating. The leading end of tube 10 is tapered (FIG. 9) and the forward end of everting tube 12 is fused or welded to the outer surface of tube 10 at the leading end along with a protective cap 24. The trailing end of tube 10 is bonded to the extension tube 14, conveniently also of polyurethane and having an outside diameter of 3.8 mm., an inside diameter of 3.12 mm. and a length of 0.6 meters.

Everting tube 12 is likewise extruded in polyurethane and has, for example, an outside diameter of 1 mm., a wall thickness of 1/15 mm. and a length of 1.6 meters. This tube has its outer surface covered with a friction reducing hydromer coating, and after extrusion, is heat set to provide an indented cross-sectional profile, preferably a substantially U-shaped profile, as shown in FIGS. 2 and 3, although other indented profiles such as a cruciform profile are also considered suitable. Heat setting of tube 12 may, for example, be effected by winding the tube around a helically grooved or ridged heated drum, whereby the ridge in the drum provides the required indentation in tube 12.

As indicated, the forward end of tube 12 is opened out, turned back on itself and welded or fused to the leading end of tube 10 at point 10a under protective cap 24, while the main body of tube 12, the uneverted length or inner wall, is taken back through tube 10 and its rear end is bonded around the opening at the forward end of an axially moveable plastic support tube 26. This forward end of tube 26 is also tapered and provided with a slit section 28 formed from one or more slits which serves as a valve arrangement for preventing tube 12 from being pushed back through tube 28. The flaps so created by the slit or slits are inwardly deflected by the pressure in the annulus thus producing an obstruction to rearward motion of the secondary tube. Further, the forward end of tube 26 is provided with caps 30 and 32 serving to prevent tube 12 from working back along the space between tubes 14 and 26. The rear end of support tube 26 is attached to a sliding metal coupling arrangement 34, to the rear of which is welded a steel tube 36 which extends back through the manifold 16 and carries a connection 38 for the syringe 20.

Extension tube 14 is at its rear end attached to a metal coupling 40 connected to the manifold and the manifold has passages 42 and 44 connected respectively to syringe 18, via a tap 46, and pressure gauge 22. Syring 18, thus, communicates via passage 42, coupling 40 and extension tube 14 with the interior of primary catheter tube 10, i.e., with the annular space surrounding the inner wall of the everting tube 12.

Operation of the device is as follows:

With the everting tube 12 and steel tube 36 in the fully retracted condition, tube 10 is introduced into the vascular system at a suitable entry point and worked through a blood vessel in the conventional manner under fluoroscopic observation until it is advanced to its full length or until an obstruction is encountered or until friction impedes its further advance. Then, steel tube 36 is advanced slightly to provide slack in the everting tube. Pressure at about 1.7 to 2 atmospheres is applied to the annular space surrounding the inner wall of tube 12 through syringe 18, causing eversion of tube 12 from the leading end of tube 10 until the slack in tube 12 is taken up, this process again being performed under fluoroscopic observation. The fluid used for everting tube 12 is conveniently a standard X-ray contrast media which allows the outline of tube 12 to be viewed under X-ray. Tube 12 thus extends from the leading end of tube 10, and when the slack in tube 12 is taken up, the steel tube 36 is further advanced and the process is repeated. This procedure is continued until the everting tube has reached its maximum extension, or until the target region of the blood vessel has been reached.

During eversions of tube 12, when pressure is applied through syringe 18, the inner wall or uneverted section of tube 12 retains its indented cross-sectional profile, FIGS. 2 and 3, while the everted outer wall is expanded to the normal substantially circular cross-section of the tube.

When the maximum or required degree of eversion has been obtained, pressure in the annular space surrounding the inner wall of tube 12 can be relaxed and the inner passageway of tube 12 is then available for the application of fluid under pressure to the target region of the blood vessel via the steel tube 36 and syringe 20. Under the influence of such pressure fluid, the inner wall of tube 10 is then expanded to its normal, substantially circular cross-section, as shown in FIGS. 5 and 6. Alternatively the everting tube can be used to transport any object through the blood vessel for diagnostic or other purposes e.g., a catheter guide wire or a small fluid sampling tube.

After treatment has been terminated, the catheter can be withdrawn by releasing pressure from both syringes, retracting steel tube 36, so that tube 12 is itself again retracted into tube 10 and then withdrawing tube 10 from the blood vessel in the normal way.

It will be appreciated that a catheter assembly as herein described and its method of application, is suitable for use in effecting entry to relatively inaccessibly regions of the vascular system for either therapeutic or diagnostic purposes. Where the catheter is to be used for treating stenoses by physical expansion of the vessel in the region of the stenoses, tube 12 may be provided with sections of differing diameter and in use, the apparatus can be manipulated in such a way that a diameter suited to expand a particular region of the vessel is available for use at the required location and the tube 12 being expansible under elevated pressure for this purpose.

Advantages of attaching the secondary tube to the distal end of the primary tube as opposed to having it originate from outside the body are two-fold: (a) there is less required distance for the secondary tube to be everted e.g., 0.3 m as to 1.3 m and therefore far less friction build-up and required everting pressures, (b) the reduced required travel of the proximal end of the secondary tube makes practical an axial feed arrangement (as opposed to winding the secondary tube on a drum) which in turn enables the lumen of the secondary tube to remain open more reliably.

While only a single embodiment of this invention has been described in detail, it will be appreciated that numerous modifications are envisaged within the scope of the invention as defined in the appended claims.

The embodiments of the invention in which an exclusive property or privilege is claimed are defined as follows:

1. The method of gaining access to a relatively inaccessible region of a blood vessel comprising entering the vascular system with the leading end of a primary flexible catheter tube, at a point of entry remote from said region, working the primary catheter tube through the vascular system so that its leading end approaches said region and then everting a second flexible catheter tube contained within said primary tube from the leading end of the primary tube to approach more closely to said region.

2. The method as claimed in claim 1 including the step, when said second tube has been everted to a required extension from the leading end of said primary tube, of using the interior passageway of said second tube for passing fluid between said point of entry and said region of the blood vessel.

* * * * *

UNITED STATES PATENT AND TRADEMARK OFFICE
CERTIFICATE OF CORRECTION

PATENT NO. : 4,437,857
DATED : March 20, 1984
INVENTOR(S) : Seth R. Goldstein, et al.

It is certified that error appears in the above-identified patent and that said Letters Patent is hereby corrected as shown below:

Column 4, lines 13 and 14, change "hydromer" to -- Hydromer ® --

Signed and Sealed this

Fifth Day of April, 1988

*Attest:*

DONALD J. QUIGG

*Attesting Officer*  *Commissioner of Patents and Trademarks*